United States Patent [19]

Blake et al.

[11] Patent Number: 4,805,876
[45] Date of Patent: Feb. 21, 1989

[54] SURGICAL STAPLE REMOVER

[75] Inventors: Joseph W. Blake, 88 Main St., New Canaan, Conn. 06840; Paul C. Di Cesare, New Canaan, Conn.

[73] Assignees: Joseph W. Blake, III, New Canaan, Conn.; Jack W. Kaufman, Merrick, N.Y.

[21] Appl. No.: 456,160

[22] Filed: Jan. 6, 1983

[51] Int. Cl.$^4$ .............................................. B25C 11/00
[52] U.S. Cl. .................................................... 254/28
[58] Field of Search .............. 30/341; 254/28; 81/419, 81/425 A, 428 R

[56] References Cited

U.S. PATENT DOCUMENTS

| 923,734 | 6/1909 | Tindall | 30/341 |
| 2,079,672 | 5/1937 | Allen et al. | 254/28 |
| 4,026,520 | 5/1977 | Rothfuss et al. | 254/28 |

Primary Examiner—Frederick R. Schmidt
Assistant Examiner—Judy J. Hartman
Attorney, Agent, or Firm—Peter C. Richardson; Lawrence C. Akers; Harold W. Ordway

[57] ABSTRACT

A surgical staple remover comprises first and second handle elements pivotally connected to each other. The front portion of the first handle element terminates in a pair of outwardly extending anvil sections having outside surfaces that diverge away from each other in the front to rear direction so that different size staples may be received thereon until the staples contact the diverging outside surfaces thereof. A blade section on the front portion of the second handle element is constructed and arranged for movement toward and away from the anvil sections, and the blade section has a lower concavely curved staple engaging edge. The curved edge engages a staple on the anvil sections with a downward and rearward force to produce a U-shaped bend in the crown of the staple to thereby facilitate its removal.

8 Claims, 2 Drawing Sheets

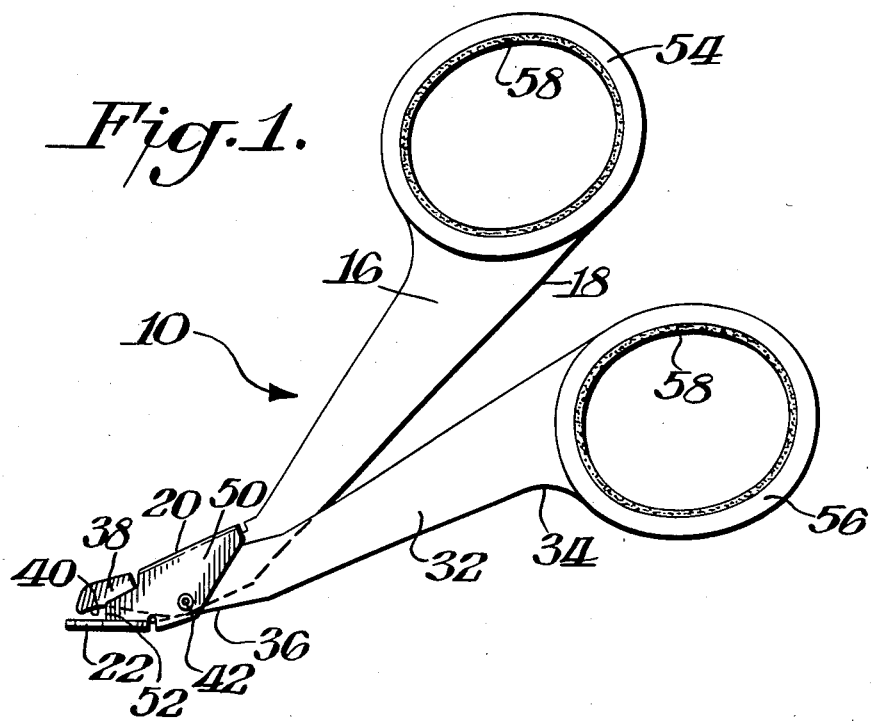
Fig. 1.
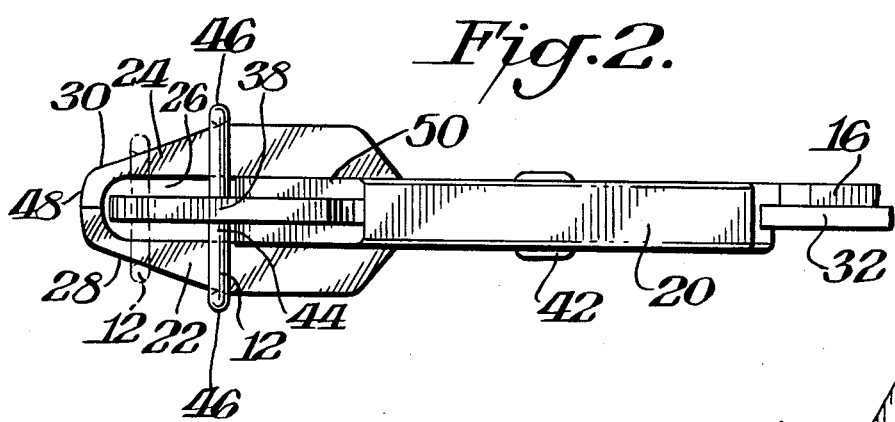
Fig. 2.
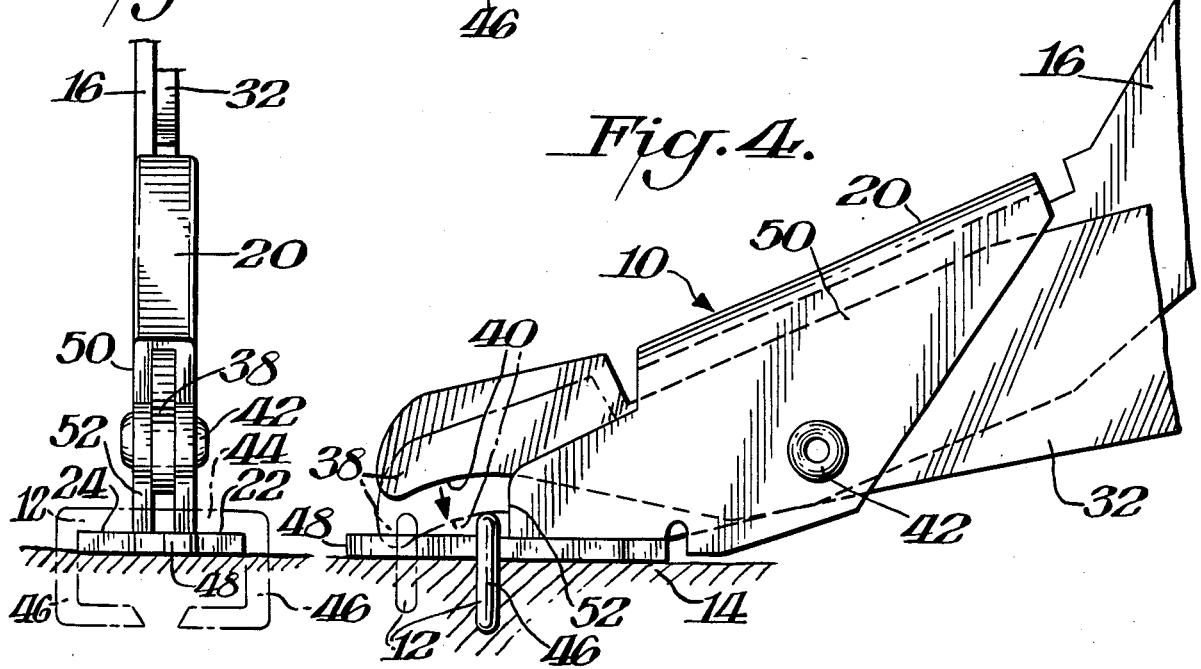
Fig. 3.
Fig. 4.

SURGICAL STAPLE REMOVER

BACKGROUND OF THE INVENTION

The present invention relates to a staple remover, and more particularly to a manually operated device for removing surgical staples from the skin.

Surgeons are turning more and more frequently to the use of surgical staples, rather than conventional thread sutures, for closing wounds or incisions in the skin of a patient because the stapling operation is often simpler when compared to thread suturing. More important, however, is the fact that stapling is much faster than thread suturing, and in those instances where a considerable amount of suturing is required, the length of time for the suturing operation and thus the length of time the patient must be maintained under anesthesia are greatly reduced when surgical staples are used.

Typical surgical staples are illustrated in U.S. Pat. Nos. 3,643,851 and 3,837,555. A staple of this type initially has an elongated crown terminating in a downwardly depending portion whose free ends are provided with downwardly and outwardly sloping cuts, forming points. During the forming and implanting of such a staple in the skin of a patient, end portions of the elongated crown are bent downwardly. This forms a staple with a narrower crown and L-shaped legs, the pointed ends of which are opposed.

The type of staple described above may be removed from the skin of a patient by bending the staple crown into a U-shaped configuration. This causes the L-shaped legs of the staple to shift upwardly and outwardly so that they may be lifted away from the patient's skin.

Heretofore proposed manual removers for bending the crown of a surgical staple and lifting the staple from the patient's skin typically comprise a pliers-like tool having first and second handles pivoted together and formed of sheet metal. The first handle terminates in a pair of spaced apart anvils provided at their rearward ends with notches so that when the anvils are slipped under the crown portion of a surgical staple, the crown will be received in the notches.

The second handle generally is provided with a relatively thick, two-ply, blade-like forward end substantially as long or longer than the anvils. The anvils have projections extending towards one another to guide the blade-like forward end between them. When the handle elements are in their open position, this blade lies above the anvils and the notches therein. As the handle elements are moved to their closed position, the blade element passes between the anvils and the notches therein making the above described U-shaped bend in the staple crown located in the notches.

Another prior art manually operated surgical staple extractor has been proposed in U.S. Pat. No. 4,026,520 which is in the form of a pliers-like tool having first and second handle elements pivotally joined together near their forward ends. These handle elements are manually shiftable between open and closed positions and may be biased to their open position.

The first handle element is bifurcated at its forward end, the bifurcations terminating in a pair of elongated anvils in parallel spaced relationship. The forward ends of the anvils are angled toward each other with the front-most tips being contiguous or nearly so. At their rearward ends, the anvils are provided with aligned notches to receive the crown of a staple. The bifurcations of the first handle element provide a steep upwardly and rearwardly sloping surface adjacent each of the anvil notches to assist in and assure the location of a staple crown in the notches.

A thin blade means is located between the bifurcations of the first handle element and is operatively connected to the forward end of the second handle element. The blade means has a nose portion shorter than the anvils and a lower edge adapted to produce a U-shaped bend in the crown of a staple located in the anvil notches. The blade nose portion is shiftable by the second handle element between a first position when the handle elements are in their open position, wherein the lower edge of the nose lies above the anvils and the notches therein, and a second position when the handle elements are in their closed position, wherein the nose lies between the anvils with the lower edge of the nose located below the anvils.

The problem with this latter prior art construction is that it, also, does not overcome all of the earlier disadvantages. For example, the front end portion of the anvils must be inclined and positioned with considerable precision in order to perform their intended purpose, i.e., to guide the blade, as do the transverse anvil projections of the art prior thereto. The extractor must be urged to open position by a biasing means whose presence complicates the construction and may become dislocated, tending to jam the extractor. Also, the more or less planar finger-engaging portions of this tool do not offer very reliable assurance against slippage of the surgeon's fingers, which may lead to slippage of the extractor, pulling on the staple and pain to the patient.

Still another type of manually operated surgical staple remover is described in copending U.S. patent application Ser. No. 311,882, filed Oct. 15, 1981 now U.S. Pat. No. 4,515,348 in the name of Joseph W. Blake and entitled "Skin Staple Extractor." Notches in the spaced apart anvils function to receive the staples and prevent them from rolling during the extraction process. A blade provided with a convexly curved lower edge moves toward and away from the anvils to produce a U-shaped bend in the crown of a staple located in the anvil notches. Also, the finger engaging portions of the extractor comprise finger gripping eyelets which serve to lessen the danger of finger slippage when compared to pliers-type devices.

SUMMARY OF THE INVENTION

Accordingly, it is an object of the present invention to provide an improved manually operated surgical staple remover which is highly reliable in operation, simple in construction, inexpensive to produce, and simple to use.

Another object of the present invention is a surgical staple remover which accommodates a wide variety of staple sizes.

In accordance with the present invention, a surgical staple remover comprises a first handle element having a rear portion and a front portion that terminates in a pair of outwardly extending anvil sections. Portions of the anvil sections are separated from one another by a slotted opening. Moreover, the anvil sections have outside surfaces that diverge away from each other in the front to rear direction whereby different size staples may be received thereon until the staples contact the diverging outside surfaces thereof. The remover further includes a second handle element having a rear portion and a front portion provided with a blade section constructed and arranged for movement toward and away from the anvil sections and into and out of the slotted opening therebetween. The blade section has a lower concavely curved staple engaging edge. Pivot means connect together the first and second handle elements so that the concavely curved edge of the blade section moves toward the anvil sections and through the slotted opening when the rear portions of the handle elements are moved toward each other. Such action causes the curved edge of the blade section to engage a staple on the anvil sections with a downward and rearward force.

Preferably, the outwardly extending anvil sections are disposed in a plane and the pivot means is rearward of the anvil sections but relatively close to the plane thereof. Also, the most forward portions of the anvil sections contact each other to thereby form a closed front tip.

An upstanding wall may be provided on the first handle element immediately rearward of the anvil sections and forward of the pivot means to thereby limit rearward movement of a large staple positioned on the anvil sections. Moreover, the rear portion of each of the first and second handle elements may be provided with a finger-receiving ring, and at least the inside of each finger-receiving ring may include a soft liner. The handle elements and pivot means may be fabricated of stainless steel.

BRIEF DESCRIPTION OF THE DRAWING

Novel features and advantages of the present invention in addition to those mentioned above will become apparent from a reading of the following detailed description in conjunction with the accompanying drawings wherein:

FIG. 1 is a side elevational view of a surgical staple remover according to the present invention, the remover being in its open position;

FIG. 2 is an enlarged fragmental top plan view of the surgical staple remover of FIG. 1 with a staple positioned on the anvil sections and a smaller staple illustrated in phantom outline;

FIG. 3 is an enlarged front end elevational view of the surgical staple remover shown in FIG. 1;

FIG. 4 is an enlarged side elevational view of the surgical staple remover shown in FIG. 1 with the curved blade thereof also shown in phantom outline at its initial point of contact with a staple.

DETAILED DESCRIPTION OF THE INVENTION

Figure 5:
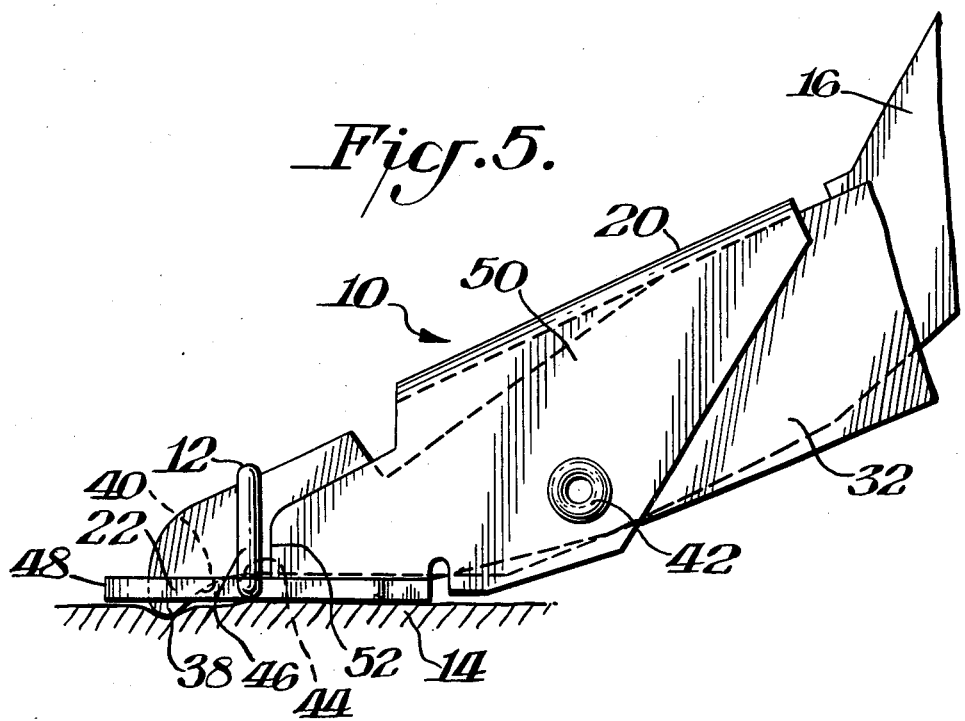
FIG. 5 is an enlarged side elevational view similar to FIG. 4 illustrating the blade section in its fully closed position and the staple removed.

Referring in more particularity to the drawing, the various figures illustrate a surgical staple remover 10 for extracting a staple 12 from the skin 14 of a patient. The remover 10 comprises a first handle element 16 having a rear portion 18 and a front portion 20 terminating in a pair of outwardly extending anvil sections 22,24. As shown best in FIG. 2, portions of the anvil sections 22,24 have outside surfaces 28,30 that diverge away from each other in the front to rear direction for the purpose of accommodating different size staples on the anvil sections, as explained more fully below.

The surgical staple remover 10 also includes a second handle element 32 having a rear portion 34 and a front portion 36 provided with a blade section 38 constructed and arranged for movement toward and away from the anvil sections 22,24 and into and out of the slotted opening 26 therebetween. The blade section 38 has a lower concavely curved staple engaging edge 40 as shown best in FIGS. 4 and 5.

A pivot in the form of a rivet 42 connects together the first and second handle elements 16,32 which enables the concavely curved edge 40 of the blade section 38 to move toward the anvil sections 22,24 and through the slotted opening 26 when the rear portions 18,34 of the handle elements 16,32 are moved toward each other. Such action causes the curved edge 40 to engage the staple 12 positioned on the anvil sections 22,24 with a downward and rearward force to thereby produce a U-shaped bend in the crown 44 of the staple 12 as is known in the art and partially shown in FIG. 5.

The outwardly extending anvil sections 22,24 of the surgical staple remover 10 are preferably disposed in a plane, perpendicular to the plane of handle elements 16,32, and the pivot point or rivet 42 is positioned rearward of the anvil sections 22,24 but relatively close to the plane thereof. With the rivet 42 located close to the plane of the anvil sections 22,24, minimal sliding action occurs between the concavely curved blade edge 40 and the crown 44 of the staple 12 during the crimping and removal operation. Since the effect of sliding contact between the blade 38 and the staple 12 tends to spin the staple outwardly, minimizing such sliding action produces the beneficial result of minimizing any tendency for the staple to so spin.

Spinning of the staple 12 during the extraction process is also eliminated by the force generated by the concavely curved blade edge 40 when it engages the staple crown 44. With the staple 12 positively positioned on the anvil sections 22,24 and the side portions of L-shaped legs 46 of the staple 12 positively engaging the diverging outside surfaces 28,30, further rearward movement of the staple 12 on the anvil sections 22,24 is impossible. Accordingly, since the concavely curved blade surface 40 produces a force on the staple crown 44 which is both downward and rearward, the staple 12 is crimped without any forward or rearward movement on the anvil sections 22,24. The blade 38 produces a U-shaped bend in the crown 44 of the staple 12 which causes the L-shaped legs 46 to lift upwardly and outwardly away from the patient's skin 14.

The most forward portions of the anvil sections 22,24 contact each other to thereby form a closed and narrow front tip 48. The closed tip 48 facilitates insertion of the anvil sections 22,24 under the crown 44 of a staple 12 to be removed.

The front portion 20 of the first handle element 16 is bifurcated, thereby forming an inverted U-shaped section 50 with the anvil sections 22,24 extending outwardly from the lower extremes of that section 50. The most forward portion of each side of the inverted U-shaped section 50 defines an upstanding wall 52 immediately rearward of the diverging anvil sections 22,24 but forward of the pivot 42. Each wall 52 functions to limit rearward movement of a stale 12 positioned on the anvil sections 22,24, in those instances where the staple crown 44 is somewhat wider than the widest span of the diverging outside surfaces 28,30 of the anvil sections 22,24. Under these conditions, the L-shaped legs 46 of such a staple will not engage the outside surfaces 28,30, but rearward movement of the staple 12 is prevented by contact with the upstanding walls 52.

As shown best in FIG. 1, the rear portion 18,34 of each of the first and second handle elements 16,32 has a finger-receiving ring 54,56 to facilitate manipulation of the remover. This arrangement functions to lessen the danger of finger slippage when compared to pliers-type devices. Preferably, at least the inside surface of each finger-receiving ring 54,56 includes a soft liner 58 fabricated, for example, from thermoplastic material.

The surgical staple remover 10 of the present invention may be made of stainless steel or the like, fabricated by stamping or other techniques known in the art. When made of such materials, the remover may be sterilized and reused. However, the remover may be made as a single-use, disposable item from any suitable noncorrosive material such as synthetic plastic and the like.

As described above, operation of the surgical staple remover 10 is quite simple but extremely effective in the removal of staples 12 from the skin 14 of a patient. Initially, the first and second handle elements 16,32 are spread apart at the rear portions 18,34 thereof until the blade section 38 engages the bight of the inverted U-shaped section 50, as is clear from FIG. 4. Next, the front tip 48 of the remover 10 is inserted under the staple crown 44 until the legs 46 of the staple 12 engage the outside diverging surfaces 28,30 of the anvil sections 22,24. After the staple 12 is firmly wedged against the anvil sections 22,24, the finger-receiving rings 54,56 are moved together causing the concavely curved edge 40 of the blade section 38 to engage the crown 44 of the staple 12. Continued movement of the finger-receiving rings 54,56 toward one another causes the blade section 38 to impart a downward and rearward force on the staple 12 as the blade 38 moves in a downward direction through the slotted opening 26 between the anvil sections 22,24. Such movement produces a U-shaped bend in the crown 44 of the staple 12, thereby causing the staple legs 46 to swing upwardly and outwardly away from the patient's skin 14. Downward movement of the blade section 38 continues until the second handle element 32 engages the underside of the bight portion of the inverted U-shaped section 50, such position being shown in FIG. 5. Finally, the staple remover 10 is positioned away from the patient and the blade section 38 is moved to its open position away from the anvil sections 22,24. The crimped staple 12 is removed from the anvil sections 22,24 and the device is ready for removal of the next staple.

We claim:

1. A surgical staple remover comprising a first handle element having a rear portion and a front portion terminating in a pair of outwardly extending anvil sections, portions of which are separated from one another by a slotted opening, the anvil sections having outside surfaces that diverge away from each other in a front to rear direction whereby different size staples may be received thereon until the staples contact the diverging outside surfaces thereof, a second handle element having a rear portion and a front portion provided with a blade section constructed and arranged for movement toward and away from the anvil sections and into and out of the slotted opening therebetween, the blade section having a lower concavely curved staple engaging edge, and means pivotally connecting together the first and second handle elements whereby the concavely curved edge of the blade section moves toward the anvil sections and through the slotted opening when the rear portions of the handle elements are moved toward each other to cause the curved edge to engage a staple on the anvil sections with a downward and rearward force and thereby crimp the staple without forward or rearward movement of the staple on the anvils.

2. A surgical staple remover as in claim 1 wherein the outwardly extending anvil sections are disposed in a plane and the pivot means is rearward of the anvil sections but relatively close to the plane thereof.

3. A surgical staple remover as in claim 1 wherein the anvil sections contact each other forward of the slotted opening to thereby form a closed front tip.

4. A surgical staple remover as in claim 1 including upstanding wall means on the first handle element immediately rearward of the anvil sections and forward of the pivot means to thereby limit rearward movement of a staple positioned on the anvil sections.

5. A surgical staple remover as in claim 1 wherein the rear portion of each of the first and second handle elements is provided with a finger-receiving ring.

6. A surgical staple remover as in claim 5 wherein at least the inside of each finger-receiving ring includes a soft liner.

7. A surgical staple remover as in claim 1 wherein the front portion of the first handle element is an inverted U-shape in cross section and the pair of anvil sections extend outwardly from the front portion of the first handle element at the lower extremes thereof.

8. A surgical staple remover as in claim 1 wherein the handle elements and pivot means are of stainless steel.

* * * * *